United States Patent [19]
Kuhns

[11] Patent Number: 5,981,171
[45] Date of Patent: Nov. 9, 1999

[54] DIAGNOSTIC ASSAYS USING NUCLEIC ACID PROBES

[75] Inventor: Mary C. Kuhns, Vernon Hills, Ill.

[73] Assignee: Abbott Laboratories, Abbott Park, Ill.

[21] Appl. No.: 07/550,250

[22] Filed: Jul. 6, 1990

Related U.S. Application Data

[63] Continuation of application No. 07/002,838, Jan. 9, 1987, abandoned.

[51] Int. Cl.$^6$ .............................. C12Q 1/70; C12Q 1/68; C12P 19/34
[52] U.S. Cl. .................................. 435/5; 435/6; 435/91.1
[58] Field of Search .................... 435/5, 6, 91.1, 435/91.2, 183; 436/94; 536/23.1, 24.3, 24.31, 24.33, 25.3; 935/8, 1, 26.77

[56] References Cited

U.S. PATENT DOCUMENTS

| | | | |
|---|---|---|---|
| 4,407,942 | 10/1983 | Birboim | 435/6 |
| 4,581,333 | 4/1986 | Kourilsky et al. | 435/6 |
| 4,683,195 | 7/1987 | Mullis et al. | 435/6 |
| 4,683,202 | 7/1987 | Mullis | 435/91 |
| 4,734,363 | 3/1988 | Dattagupta et al. | 435/91 |
| 4,766,062 | 8/1988 | Diamond et al. | 435/6 |
| 4,766,064 | 8/1988 | Williams et al. | 435/6 |
| 4,894,228 | 1/1990 | Purcell et al. | 424/89 |

FOREIGN PATENT DOCUMENTS

| | | | |
|---|---|---|---|
| 0097373 | 4/1984 | European Pat. Off. | C07H 21/00 |
| 0153873 | 4/1985 | European Pat. Off. | |
| 0133671 | 6/1985 | European Pat. Off. | C12Q 1/68 |
| 8403285 | 8/1984 | WIPO | C07H 17/00 |

OTHER PUBLICATIONS

Stratagene Catalog, p. 158, 1997.
Pharmacia Gel Filtration Pamphet, Published Dec. 1984.
Mc Ghee et al Biochemistry 16 (15) 3267–76 (1977).
Ashley et al Analytical Biochemistry 140(1): 95–103 (1984).
Sanger et al Proc Natl Acad Sci 74(12)5463–67 (1977).
Manning et al Biochemistry 16(7) pp. 1364–1370 (1977).
Hayes et al Analyt. Biochem 116 pp. 480–488 (1981).
Hames et al Nucleic Acid Hybridisation (1985) IRL Press LTD Oxford, England.
Lehninger, Biochemistry Worth Publishers Inc N.Y., N.Y. (1970) pp. 153–155.

*Primary Examiner*—Kenneth R. Horlick
*Attorney, Agent, or Firm*—Thomas D. Brainard; Paul D. Yasger

[57] ABSTRACT

Methods and compositions are provided for a rapid quantitative nucleic acid hybridization assay for detecting a DNA or RNA sequence in a biological sample. The method comprises solution hybridization of a target nucleic acid sequence with a detectably-labeled probe, separation of the target-nucleic acid probe from the unhybridized probe by gel exclusion or affinity chromatography and detection of the amount of labeled probe as an indication of the target nucleic acid present in the biological sample.

24 Claims, 2 Drawing Sheets

DIAGNOSTIC ASSAYS USING NUCLEIC ACID PROBES

This application is a continuation of application Ser. No. 07/002,838, filed Jan. 9, 1987, abandoned.

BACKGROUND OF THE INVENTION

1. Field of the Invention

This invention relates to methods and compositions for detecting nucleic acid sequences including deoxyribonucleic acid (DNA) or ribonucleic acid (RNA) ["target nucleic acids" or "target nucleic acid sequence"] in a biological sample. The method permits the rapid determination of the presence of specific DNA or RNA sequences in the biological sample by hybridizing labeled DNA or RNA probes with the target nucleic acids in a solution. Following hybridization of the labeled probes to the target nucleic acid, the resulting hybridized and non-hybridized probes are separated by gel exclusion or affinity chromatography. The methods of this assay are suitable for use with biological samples, such as crude serum, plasma or tissue culture cells or tissue extracts or with purified or partially purified samples.

2. Description of the Prior Art

The nucleic acids DNA and RNA contain linear sequences of purine and pyrimidine bases which have the ability to form hydrogen bonds resulting in double-stranded helical regions. The process of forming a double-stranded hydrogen bonded helical region is referred to as hybridization or DNA renaturation. Such hybridization occurs when DNA or RNA samples containing complementary sequences are incubated under proper salt, pH and temperature conditions. Any two nucleic acid sequences can hybridize with one another, i.e., DNA:DNA, RNA:RNA or RNA:DNA, as long as they have a complementary nucleotide sequence. The rate of double helix formation is a function of both the concentration of reactants and the temperature. When one of the two nucleic acid chains contains a known sequence and a label, then the presence of a complementary nucleic acid sequence in an unknown solution can be determined by hybridization and detection of the label.

DNA probes labeled with radioisotopes have been widely used to localize specific nucleic acid sequences in mixtures of DNA restriction fragments fractionated by gel electrophoresis. A replica of a gel electrophoresis pattern is made by transferring fractionated DNA fragments to a sheet of nitrocellulose paper either by electrophoresis or by diffusion in a process called blotting. By hybridizing a radioactive probe to DNA or RNA bound to the nitrocellulose paper, hybrids are formed between the probe and the specific DNA sequence sought. Unhybridized probe is washed away and labeled areas of the nitrocellulose paper are detected as by autoradiography.

Another blotting method adapted to detect hepatitis B viral DNA in serum or plasma was described by Scotto et al., *Hematology*, 3:279–284 (1983). This method permits use of a larger sample volume of unextracted serum or plasma by binding sample DNA directly to nitrocellulose paper using a vacuum filtration apparatus.

The methods described above rely on binding the target nucleic acid sequences to a solid phase, such as nitrocellulose paper, then removal of unhybridized labeled probe by washing and detection of labeled probe hybridized with target nucleic acid sequences bound to the solid phase. These solid phase methods can result in extensive loss of sample, are time-consuming and involve numerous steps including solid phase preparation, binding, blocking and washing.

The procedures presently available for preparation of sample, hybridization and separation of hybridized probe from unhybridized probe are not generally suitable for routine use due to either the complexity of the procedures requiring highly trained personnel, the time-consuming nature of the procedure or the need for specialized equipment. There has been a need for a simple method which shortens the time required to perform the assay, requires a minimum quantity of materials, is reliable and reproducible and provides a method of quantitation.

Nobrega, et al., *Analytical Biochemistry*, 131:141–145, (1983) describe a method for detection of specific RNA transcripts during RNA processing wherein both the target nucleic acid and probe are in solution. In this method the free DNA probes are separated after hybridization utilizing electrophoretic migration on agarose and visualization by autoradiography.

The principle of separating small molecules from larger, higher molecular weight molecules based on differences in weight and/or conformation is known in the literature. Such methods include differential centrifugation, chromatographic methods, electrophoretic methods, dialysis and like methods.

Methods for the production of DNA containing the sequence of the hepatitis B virus genome by the cloning of the hepatitis sequence onto a bacterial plasmid are described in U.K. Patent Application No. GB 2034323A, published Jun. 4, 1980. Reagents and methods for the quantitative determination of viral DNA, such as hepatitis B virus DNA, utilizing a known amount of a phage vector was described in PCT Application No. WO 85/3951, published Sep. 12, 1985. Methods and compositions useful for detecting denatured, solid phase-affixed pathogen DNA, together with a labeled DNA probe suitable for hybridization was also described in U.S. Pat. No. 4,358,535.

SUMMARY OF THE INVENTION

The invention provides methods and compositions for a rapid quantitative assay for detecting a target nucleic acid sequence in a biological sample. The method comprises providing a biological sample containing a target nucleic acid capable of hybridizing with a nucleic acid probe in a liquid medium. The target nucleic acid sequence is then combined with a labeled nucleic acid probe. The hybridized and unhybridized probes are separated by gel exclusion or affinity chromatography. The amount of hybridized probe is determined following the separation step as a measure of the amount of target nucleic acids present in the biological sample. Compositions of probes useful in the inventive method comprise specific DNA or RNA sequences which are stably associated with a detectable label, such as a radioisotope, an enzyme, a radiopaque substance, a fluorescer, a chemiluminescent molecule, liposomes containing any of the above substances, or a specific binding pair member. The labeled nucleic acid probe is complementary to a target nucleic acid sequence and has an effective molecular weight or specific binding pair member such that hybridized probe is readily separated from unhybridized probe by gel exclusion or affinity chromatography. Also disclosed are novel methods of preparation of probes for use in the inventive assay.

Kits for use in determining the presence of a target nucleic acid sequence in a biological sample contain a nucleic acid probe stably associated with a detectable label and a gel exclusion or affinity column chromatography apparatus suitable for separating unhybridized probe from probe hybridized to the target nucleic acid sequence.

DETAILED DESCRIPTION OF THE INVENTION

Definitions

Figure 1:
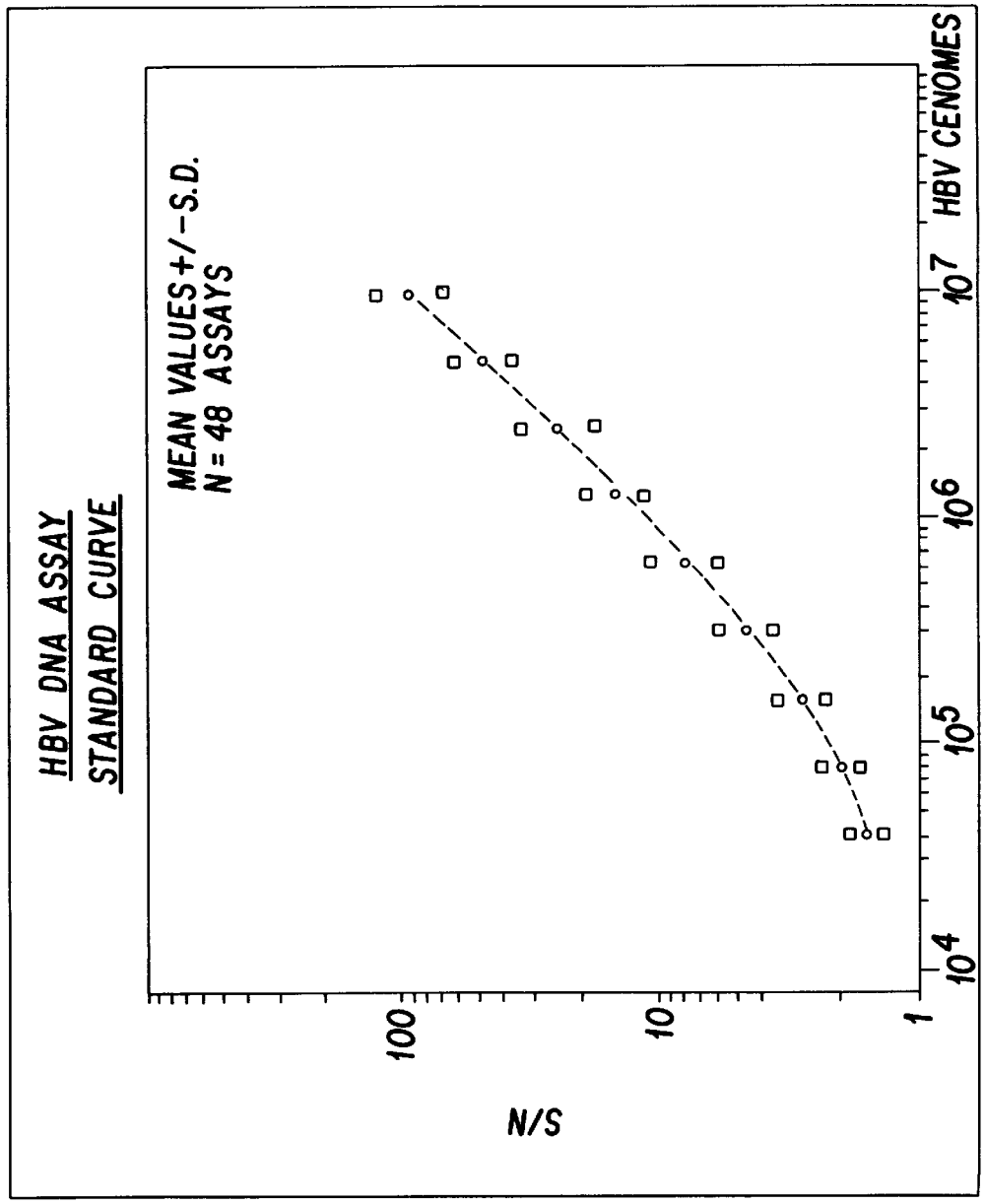
FIG. 1 shows a log—log plot of a hepatitis B virus DNA assay standard curve comparing on the X-axis the number of hepatitis B virus genomes and on the Y-axis the sample counts divided by the negative control sample counts.

Gel exclusion chromatography: This procedure is also known as gel filtration and comprises the use of a granular material, usually a dextran, which forms a medium wherein there are two phases. One phase is the liquid inside the granular material and the other phase is the liquid material outside the granular material. Material in solution completely excluded from entering the granular material due to its large size passes through the column first and is known as the void volume. Smaller molecules in solution are delayed by movement into the granular material and are retarded by the material as a function of their effective molecular weight. The material included in the granular material is known as the included volume. Therefore, exclusion chromatography of a mixture of smaller probe nucleic acids and larger nucleic acids hybridized with nucleic acid probes to form a duplex, results in the smaller probe nucleic acids being retarded by the granular material in the included volume and the larger hybridized duplex being excluded in the void volume. Such materials are available, for example, from Pharmacia Co. under the brand names Sephadex® and Sepharose® and from BioRad Co. under the name Biogel®.

Affinity chromatography: This procedure utilizes a column packed with an insoluble polysaccharide or a synthetic resin covalently linked to a molecule that binds specifically to a second molecule to form a specific binding pair. Exemplary specific binding pairs are an antigen-antibody, a substrate-enzyme, or biotin-avidin. A column containing resin bound to a specific binding pair member binds to and removes those molecules which bind specifically to the column's binding pair member from a crude or partially purified extract or preparation. The substance attached to the column, can be obtained by use of an eluting solution of high ionic strength, by variation of pH or like methods. The eluted substance can then be quantitated.

Specific binding pair: A specific binding pair comprises two different molecules, wherein one of the molecules has an area on its surface or in a cavity which specifically binds to a particular spatial and polar organization of another molecule. The members of the specific binding pair are often referred to as a ligand and receptor or ligand and anti-ligand. Often the receptor will be an antibody and the ligand will be an antigen. Other specific binding pairs include hormone-receptor pairs, enzyme-substrate pairs, biotin-avidin pairs and glycoprotein-receptor pairs. Also included are fragments or portions of specific binding pairs which retain binding specificity, such as fragments of immunoglobulins, including Fab fragments and the like. The antibodies can be either monoclonal or polyclonal.

Detectable labels: A label is a substance which can be covalently attached to or firmly associated with a nucleic acid probe which will result in the ability to detect and quantitate the amount of probe. Among the substances contemplated are radioisotopes such as $^3H$, $^{125}I$, $^{131}I$, $^{32}P$, $^{14}C$ and $^{35}S$; chemiluminescent molecules such as acridines or luminol; fluorescers such as fluorescein, phycobiliproteins, rare earth chelates, dansyl, rhodamine; enzyme substrates and inhibitors such as horseradish peroxidase, glucose oxidase, glucose-6-phosphate dehydrogenase, β-galactosidase, pyruvate kinase, alkaline phosphatase, acetylcholinesterase; metal particles or other radiopaque molecules such as colloidal gold, magnetic particles; liposomes containing any of the above substances; antigens, such as proteins, carbohydrates or haptenic molecules and antibodies specific for those antigens; and glycolipids or glycoproteins which are members of specific binding pairs.

Nucleic acid sequence: A nucleic acid sequence detectable by the present method is a sequence of nucleotides including ribonucleotides or deoxyribonucleotides. These nucleic acid sequences may be either single-stranded or double-stranded or partially single-stranded and partially base paired regions. Contemplated ribonucleic acid sequences include both messenger and ribosomal RNA.

Hybridization: Hybridization is the formation of a stable association through hydrogen bonding and stacking forces between nucleic acid sequences wherein the sequences are sufficiently bonded to allow separation of the hybridized and unhybridized sequences. Hybridization rate is dependent upon temperature, salt, pH levels, concentration of reactants, and presence of other molecules such as dextran sulfate.

Proteinase: A proteinase is an enzyme capable of breaking a peptide bond including both exopeptidases and endopeptidases such as protease, Proteinase K, pronase, trypsin, alkaline protease, subtilisin, or chymotrypsin.

Target nucleic acids or target nucleic acid sequences: As used herein, these terms refer to DNA or RNA, whether in single or double-stranded form, including messenger or ribosomal RNA. For example, target nucleic acids capable of detection by the inventive method are found in viruses, microorganisms, either prokaryotic or eukaryotic, and any aberrant cell that may be associated with a disease or physiologic state. Among those target nucleic acids are the nucleic acids of HIV (HTLV-III or LAV), hepatitis viruses, herpes viruses, human retroviruses, human papilloma viruses, Epstein-Barr virus, Cytomegalovirus, viral RNA transcripts, and replicative intermediates. Also included are nucleic acids of bacteria such as mycoplasmas, rickettsiae and chlamydiae and eukaryotic pathogens such as fungi, yeast and abnormal or variant host cells, particularly those containing oncogenes or genetic defects or genetic markers.

Biological sample: As used herein, a biological sample is any sample which may contain a target nucleic acid of interest. The source of the biological sample includes plants, insects and animals. Among the preferred biological samples are serum, plasma, synovial fluid, biopsy material, tissue-culture cells or growth medium from cells in tissue culture, tissue extracts and membrane washes.

Methods of Use

Methods are provided for a rapid quantitative assay of a target nucleic acid sequence utilizing a labeled nucleic acid probe. The method comprises as a first step providing a biological sample containing a target nucleic acid in a liquid medium. A crude biological sample in a liquid medium such as serum, plasma, tissue sections or extracts, lymphocytes, tissue culture cells or the supernatant growth medium from tissue culture can be used in the assay without prior purification. Alternatively, a purified or partially purified sample can be assayed. Purification steps can include separation, extraction, cell disruption or homogenization of tissue or biological fluids. Additionally, carrier nucleic acids which do not react with a probe can be added to the sample during purification to reduce non-specific loss of nucleic acid.

Next, the sample can be treated with a detergent or a proteinase in order to solubilize and release the nucleic acids for assay. The addition of a proteinase is preferred in part because that treatment results in more stable and solubilized nucleic acids. Among the proteinases considered useful in this method are Proteinase K, trypsin, chymotrypsin, pronase, alkaline proteases, lysozyme and subtilisin. Other enzymes useful in preparing target nucleic acids include DNAse when the target nucleic acid sequence is RNA; or RNAse when the target sequence is DNA.

If the target nucleic acid sequence is not present in the biological sample in single-stranded form, it must be denatured to permit hybridization with a nucleic acid probe. Denaturation can be accomplished by treatment under alkaline conditions such as addition of sodium hydroxide or by heating. When the target nucleic acid sequence is RNA, a preferred method for denaturation is thermal denaturation wherein RNA secondary structure is disrupted.

Following disruption of the target nucleic acid secondary structure to provide a single-stranded nucleic acid, the hybridization reaction with a labeled probe is performed under conditions suitable for selectively binding the labeled probe to the target nucleic acid. General methods for hybridization reactions and probe synthesis are disclosed in *Molecular Cloning* by T. Maniatis, E. F. Fritsch and J. Sambrook, Cold Spring Harbor Laboratory, 1982. The hybridization reaction can take place under a number of pH, salt and temperature conditions. The pH can vary from 6 to 9 with a preferred pH being 6.8 to 8.5. The salt concentration can vary from 0.15 M sodium to 0.9 M sodium. Other cations can be utilized as long as the ionic strength is equivalent to that specified for sodium. The temperature of the hybridization reaction can vary from 30° C. to 80° C. with a preferred temperature range between 45° C. and 70° C. Additionally, other compounds can be added to the hybridization reaction to promote specific hybridization at lower temperatures, such as at or approaching room temperature. Among the compounds contemplated for lowering the temperature requirements is formamide.

Following the hybridization reaction, the target nucleic acid hybridized to labeled probe is separated from the unhybridized labeled probe to determine the quantity of hybridized probe and thus of target nucleic acid present in the sample by gel exclusion or affinity chromatography. The preferred method of separation is accomplished by gel exclusion chromatography. The conditions for the separation method must be such that the hybridized target nucleic acid and detectable probe remain bound to each other. The separation solution may contain inhibitors of nucleases and, also, additional carrier nucleic acid sequences which do not interact with the probe.

Among the preferred methods of separating the hybridized probe from the unhybridized probe are gel exclusion chromatography through matrices composed of polyacrylamide, sepharose, cross-linked sepharose, agarose, cross-linked agarose or other similar materials. Products suitable for such gel exclusion chromatography include the Pharmacia Sephadex® products designated G50, G100, G200, Pharmacia products designated Sepharose® CL2B, 4B, 6B, S-200, S-400 and S-1000. Other suitable products from the BioRad Corporation include P-20, P-60, P-100, P-200, A-0.5 m and A-1.5 m.

The object of the separation reaction is to permit the differential detection of the quantity of probe bound to the target nucleic acid without unhybridized probe causing an excessive background level which prevents precise detection of hybridized probe. Therefore, the target nucleic acid in combination with the detectable probe must be of a size or conformation sufficiently distinct from the detectable probe alone to allow separation to occur based on the gel exclusion chromatographic behavior of the samples. Thus, it is essential that the length of the labeled nucleic acid probe is carefully controlled by methods described in greater detail below. When the target nucleic acid is not large enough to permit separation by gel exclusion chromatography, a specific unlabeled carrier nucleic acid can be used to effectively increase the size of the target nucleic acid-probe complex.

When separation is accomplished utilizing standard gel exclusion chromatography reagents such as those contained in a kit, the volume of sample applied to the column and of the elution buffer must be carefully controlled.

Following the separation of hybridized probe from unhybridized probe, the presence of or quantity of hybridized probe is determined. The method of detection depends upon the type of label present on the probe. When the label is a radioisotope, the detection method can be by gamma or scintillation counting or by another method capable of detection such as autoradiography or photographic detection. When one member of a specific binding pair is used on the probe as the label then the second member of the pair may be used to effect detection and quantitation. The second member of the pair may itself contain a second detectable marker such as an enzyme or isotope. If the label is an enzyme or enzyme inhibitor, then reactions detecting the presence or the absence of enzymatic activity can be utilized. Preferred enzymatic reactions are those which result in a calorimetric change which can be detected utilizing a spectrophotometer. Additional labels include radiopaque substances detected utilizing electromagnetic radiation; magnetic particles detected utilizing magnetic fields; immunological methods involving using antibodies and specific antigens; fluorescent and chemiluminescent markers; and members of any specific binding pair such as glycolipids or glycoproteins.

To precisely determine the quantity of a target nucleic acid sequence present in an unknown biological sample, a positive and negative control containing a known quantity of the target nucleic acid sequence can be assayed in parallel with the sample thereby standardizing assay results.

The methods of the present invention can be used to detect the presence in a biological sample of single- or double-stranded nucleic acid DNA or RNA. Preferred target nucleic acid sequences include those associated with pathogens such as viruses, bacteria, yeast, fungi, protozoa or eukaryotic cells. Included within this class of eukaryotic cells are those of the host itself which are transformed or which contain an oncogene or a known genetic marker. Preferred among the viral pathogen nucleic acids detectable by the methods of this invention are those responsible for hepatitis, herpes, acquired immune deficiency syndrome (HIV, HTLV III or LAV), human papilloma viruses, Epstein-Barr viruses, or other viruses or organisms.

Methods of the present invention are suitable for detecting small quantities of target nucleic acids as low as 0.07 picograms of nucleic acid. Reagents facilitating the methods of the present invention can be included in kit form for use in manual assays or in automated diagnostic devices or analyzers. Methods for increasing the amount of target nucleic acid, as for example, by propagation of a virus in tissue culture or amplification of target as described in *Science,* 230:1350–1354 (1985) are compatible with the present invention.

Probe Characterization

A probe of the present invention can be either DNA or RNA complementary to a target nucleic acid to be detected. A probe of the present invention is at least 20 nucleotides in length and preferably represents between 10 and 20% of the length of a target nucleic acid in its native form. When the effective molecular weight of the target and probe molecules do not permit separation by gel exclusion chromatography, an unlabeled specific carrier DNA or RNA molecule of sufficient size to permit separation by gel exclusion chromatography can be used. The carrier molecule contains a sequence complementary to a portion of the target nucleic acid which is different from, i.e., does not overlap, cross-hybridize with or sterically interfere with probe molecule hybridization. The carrier thus can be relatively inexpensive to prepare and need not be labeled. Alternatively, the carrier can be a relatively short nucleic acid molecule containing a specific binding pair member which permits attachment to another molecule of relatively high molecular weight such as an antibody or avidin thus increasing the effective molecular weight of the probe-target complex.

The detectable labels can be radioisotopes, chemiluminescent molecules, fluorescers, enzymes, antigens or members of specific binding pairs, as discussed previously. The detectable labels can be attached to the probe after probe synthesis or they can be incorporated into the probe during synthesis, as with $^{32}P$, $^{3}H$, $^{125}I$, $^{14}C$ or $^{35}S$.

The method of the present invention includes preparation of a probe for detecting hepatitis B virus (HBV) DNA based upon primer-extension. The probe can be between 50 and 400 nucleotides in length, preferably 75 to 300 nucleotides and more preferably 150 to 250 nucleotides. The template consists of an M13 phage DNA containing an insert of cloned hepatitis B virus DNA. The single-stranded template is hybridized or annealed with a primer of at least 17 nucleotides in length which is complementary to the hepatitis B insert. The primer sequence is chosen from known sequences of hepatitis B virus which can be found in Charnay, et al., *Proc. Natl. Acad. Sci.*, 76:2222 (1979). After annealing the template and primer, the nucleotides dGTP, dCTP, dATP, and either dTTP or dUTP and the Klenow fragment of DNA Polymerase I are added. One or more nucleotide species may contain a label such as $^{125}I$. Synthesis of DNA or RNA occurs by extension of the primer resulting in a labeled copy of the inserted DNA. The length of the probe is controlled by limiting the concentration of one of the nucleotides.

For example, 72 ug of single-stranded DNA isolated from a preparation of M13 phage containing a 3200 base pair insert of hepatitis B DNA is annealed with 20 ng of a 23 base primer molecule complementary to the surface antigen region of the hepatitis B genome. Annealing is accomplished in a volume of 120 ul of 10 mM Tris pH 8.5, 10 mM $MgCl_2$ for 1 hour at 65° C. 1500 picomoles of each of the nucleotides dGTP, dTTP and DATP are added in a volume of 90 ul. 150 picomoles of dCTP are added, followed by the addition of 150 picomoles of labeled dCTP such as $^{125}I$-dCTP which is commercially available from NEN Dupont or Amersham. The dCTP concentration in the reaction is thus a limiting substrate. The Klenow fragment of DNA Polymerase I is added to a final concentration of 0.6 units/ul, and extension of the previously annealed primer proceeds for 2 hours at 15° C. The reaction is terminated by the addition of EDTA to a final concentration of 25 mM. The reaction mixture is then applied to a chromatography column containing a 3.4 ml bed volume of Sepharose® CL4B to separate unincorporated nucleotides from the newly synthesized copy DNA. The void volume containing the template and the newly synthesized copy DNA is then treated with NaOH to a final concentration of 0.15 N to denature the template and the extended primer containing the radioisotope. The denatured sample is applied to a Sepharose® CL4B gel column equilibrated with 0.03 N NaOH. Chromatography under these denaturing conditions allows the separation of the high molecular weight template from the smaller, lower molecular weight labeled extended primer. The template appears in the void volume while the labeled extended primer remains in the included volume. The fractions comprising the included volume are pooled and the pH is adjusted to neutrality with 2 M $NH_4Ac$. The neutralized, pooled fractions constitute the $^{125}I$-labeled probe. The probe is then used for assays by adding 40,000–200,000 dpm of the $^{125}I$-probe to each hybridization. The specific activity of the probe is typically at least $10^9$ dpm/ug.

Alternatively the labeled copy is separated from the template by heat denaturation followed by purification by gel electrophoresis under denaturing conditions to select probe molecules of the desired length. The length chosen depends upon the ability to separate unhybridized probe from probe hybridized to target in the assay method. Any DNA or RNA sequence of interest can be cloned in a single-stranded phage or plasmid vector and then used as a template when proper primers are used. Alternatively, the hybridization or sequencing primers flanking inserted sequences in M13 phage can be used to prime synthesis and generate a probe.

Probes of virtually any length can be prepared by the above method. This method facilitates the preparation of high yields of probes of controlled lengths. Also, at least 50% of the radioisotope label is incorporated in this method, yielding sufficient probe for about 4,000 hybridization assays by the inventive assay method described in the above example.

The data in FIG. 1 illustrates a standard curve for hepatitis B viral DNA using a $^{125}I$-labeled probe prepared as described above. The assay protocol is described in Example I. As can be seen in FIG. 1, counts of labeled hybridized probe increase in proportion to the number of viral genomes present. These methods represent an efficient reproducible process for preparing high yield single-stranded DNA probes having favorable characteristics for hybridization and separation by gel exclusion chromatography. The probe length and the specific activity of the probe are useful with crude serum or plasma and with other body fluids and cell or tissue lysates. Following hybridization of such biological samples, the separation methods result in a highly specific and highly sensitive diagnostic assay for the presence of the target nucleic acid.

Alternative methods of probe preparation include using the Riboprobe® system (available commercially from Promega Biotec) to prepare RNA probes of known length or preparing end-labeled oligomers by known methods.

A general method for end-labeling nucleic acids using $^{32}P$-nucleotides has been described in the laboratory manual *Molecular Cloning* by T. Maniatis, E. F. Fritsch and J. Sambrook (Cold Spring Harbor Laboratory, 1982) herein incorporated by reference.

Alternatively, a nucleic acid probe can be labeled with $^{125}I$ by methods known in the art. Labeled or unlabeled specific single-stranded (SS) DNA probes can be made by the method described by Jingzhong et al., *Gene*, 42:113–117 (1986), herein incorporated by reference.

Kits

Kits suitable for use in practicing the present method contain a labeled nucleic acid probe and a gel exclusion or affinity column chromatography apparatus which is suitable for separating the target nucleic acid sequence bound to the probe from the unhybridized probe. Conveniently, the kit can contain additional reagents and apparatus such as enzymes useful in preparing a biological sample, for example, Proteinase K; solutions for denaturing a target nucleic acid, such as sodium hydroxide; buffers suitable for use in a gel exclusion chromatographic separation step; and a work station containing collection tubes, a flotation rack suitable for the hybridization reaction, sample diluent, and instructions on how to perform the hybridization method.

The following examples are offered by way of illustration and not by way of limitation.

EXPERIMENTAL EXAMPLES

Example I
Determination of Hepatitis B Viral DNA in Serum and Plasma

A sample of serum or plasma (200 ul) was solubilized and denatured by the addition of 10 ul of a buffer containing Proteinase K at a minimum concentration of 10 mg/ml. Following incubation of the sample with the Proteinase K for 1 hour at room temperature, 20 ul of a solution of NaOH was added to bring the minimum NaOH concentration to 0.1 N. This resulted in denaturation of the nucleic acids contained in the sample. Alternatively, heat denaturation can be utilized with elimination of the NaOH addition and neutralization steps. Following the alkaline denaturation step, 70 ul of neutralizing buffer containing Tris-HCl was added to bring the pH to neutrality and NaCl to a final concentration of 0.5 M, and a labeled HBV probe prepared as described before was added. An acetate buffer or a phosphate buffer may be substituted for the Tris-HCl buffer. The single-stranded HBV probe was labeled with $^{125}$I, but $^{35}$S, $^3$H or other detectable markers, such as biotin or an antigen can be used. SDS can be included in the hybridization solution up to 10%. The actual hybridization reaction was carried out for 16 hours at 65° C. The sample was then loaded onto a 3.4 ml bed volume of Sepharose® CL4B with column dimensions of 0.5 cm by 20 cm. After allowing the sample to enter the gel bed, a volume of buffer containing 10 mM Tris-HCl, 1 mM EDTA, pH 8.0, was added such that the volume of the sample and added elution buffer was equal to 1.5 ml. The elution of the excluded viral DNA-probe hybrid then proceeded unattended. The elution process stops automatically and the eluted volume can be analyzed for radioactivity or the presence of other detectable markers.

Samples containing known quantities of HBV DNA as positive controls or negative controls (serum without HBV DNA) were run in parallel as standards. By comparison of the unknown sample with standard samples, a quantitative estimate of HBV in each sample can be determined. FIG. 1 shows the assay results for a serial dilution of a sample containing known concentrations of hepatitis B viral DNA evaluated by this method.

Example II
Elution Profile of Hybridized Target DNA and Labeled Probe

Figure 2:
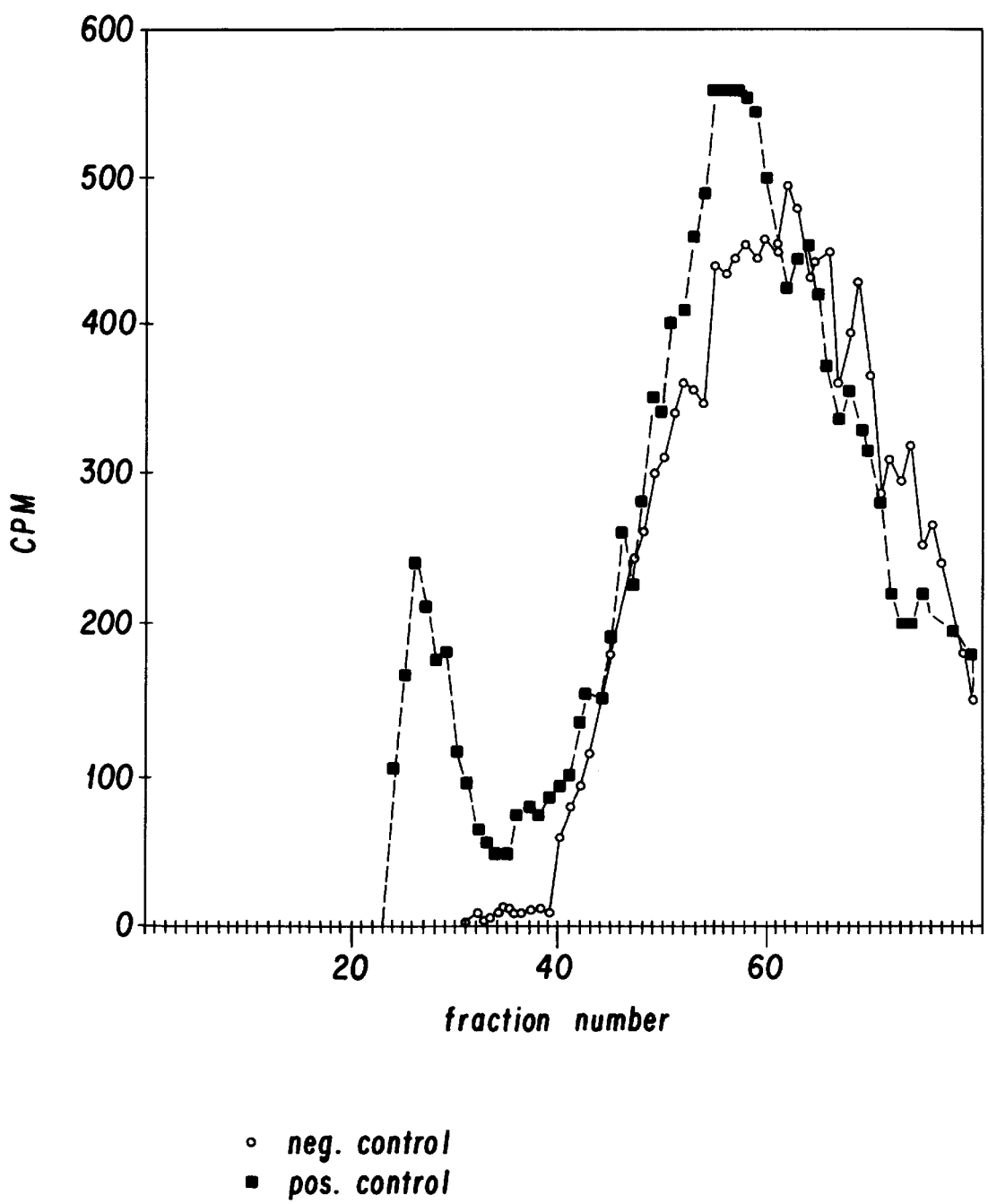
FIG. 2 shows a gel exclusion chromatograph profile wherein the void volume contains the target nucleic acid sequence hybridized to a nucleic acid probe and the included volume contains the nucleic acid probe which did not hybridize.

HBV DNA was detected in a biological sample utilizing the radioactive probe and column disclosed in Example I. The negative control consisted of a serum sample negative for hepatitis B markers. The positive control was a serum sample from a chronic carrier of hepatitis B. Hybridization as described in Example I was carried out for 16 hours at 65° C. 300 ul of hybridization mixture described in, Example I was applied to the column and eluted with buffer containing 10 mM Tris, pH 8.0 and 1 mM EDTA. FIG. 2 illustrates the elution profile from the gel exclusion chromatographic column with the target hepatitis B viral DNA and hybridized probe contained in the void volume (fractions 1–33) and unhybridized probe retarded by the column and eluted in the included volume.

Example III
Assay for HIV Specific Sequences in Tissue Culture

A) Tissue Culture Supernatant

Twenty-five ul of a solution of 120 mM vanadyl, 10% SDS and 21 mg/ml Proteinase K was added to 200 ul samples of supernatant obtained from cell cultures of lymphocytes (H9 cells) uninfected or previously infected with HIV. After incubating for one hour at room temperature, 75 ul of a probe mixture containing 0.5 M NaCl and a $^{32}$P-oligomer probe having 23 nucleotides from an HIV sequence as disclosed in Cell, 401:10 (1985) were added. An exemplary probe contained a sequence complimentary to bases 732–753. After incubating for 16 hours at 45° C., the sample was loaded onto a Sepharose® CL4B column and eluted with 1420 ul of a buffer containing 10 mM Tris pH 8.0. The total 1720 ul contained in the eluate was counted for radioactivity. A typical negative control contained 82 cpm while a typical positive control contained 3000 cpm.

B) Tissue Culture Cells

Alternatively, the cells from the culture described above can be assayed. Cell pellets containing known numbers of cells are prepared by centrifugation to remove the tissue culture medium. The cells are resuspended in 200 ul of buffer such as saline and treated as the sample described in Example III A. An additional step consisting of heat denaturation of the sample prior to hybridization can be included. The following table illustrates the counts per minute obtained from a typical assay of cells.

| Assay of Cells in Culture | | |
|---|---|---|
| | Total CPM in Eluate | |
| Cell Number | Uninfected Cells | Cells Infected with HIV |
| $10^5$ | 47 | 664 |
| $5 \times 10^5$ | 200 | 3316 |
| $10^6$ | 373 | 5541 |
| $5 \times 10^6$ | 1439 | 13435 |

C) Nucleic Acid Extracts of Tissue Culture Cells

Alternatively, the nucleic acid (DNA and/or RNA) can be extracted from tissue culture cells or supernatants by methods well known to those skilled in the art such as described by Maniatis, et al., supra, and resuspended in 200 ul 10 mM Tris buffer, pH 8.0. The sample is then treated as described in Example III B. Lymphocytes or macrophage preparations taken directly from patients may also be used. The following table illustrates the counts per minute obtained from the assay of DNA extracted from tissue culture cells.

| DNA Extracted from Tissue Culture Cells | | |
|---|---|---|
| | Total CPM in Eluate | |
| ug Total DNA | DNA from Uninfected Cells | DNA from Cells Infected with HIV |
| 0.6 | 13 | 106 |
| 3.0 | 64 | 424 |

-continued

DNA Extracted from Tissue Culture Cells

| | Total CPM in Eluate | |
|---|---|---|
| ug Total DNA | DNA from Uninfected Cells | DNA from Cells Infected with HIV |
| 6.0 | 94 | 948 |
| 30.0 | 350 | 4741 |

Example IV

Hepatitis B Viral DNA Assay Using a Biotin-Labeled Probe

An enzyme-antibody conjugate was prepared as follows: Antibody specific for biotin was conjugated by the peroxidase method described by Wilson, *Immunofluoresc. Relat. Staining Tech.*, Proc. Int. Conf., 6th edition: Knapp, Holubar, Wick, Elsevier, Amsterdam (1978) with horseradish peroxidase. A low molecular weight conjugate (MW≦250,000) was prepared by gel exclusion exclusion chromatography on A-50 M agarose. 100 ul of conjugate retained by the column was incubated at 40° C. for 12 minutes with 100 ng of M13 phage DNA containing an HBV insert in 100 ul 10 mM Tris, pH 8.0, previously hybridized for 25 minutes at 65° C. with 5 ng of a nick translated HBV-specific probe containing biotinylated UTP. The negative control consisted of 100 ul 10 mM Tris, pH 8.0, containing no HBV sequences and treated as described for the positive control. The samples were then applied to a column containing a 10 ml bed volume of agarose A-50 M (available commercially from BioRad) and 100 ul fractions were eluted. Fraction 22 was collected. 250 ul of a solution of OPD (orthophenylenediamine) in citrate-phosphate buffer containing hydrogen peroxide was added. That mixture was incubated for 4 minutes at room temperature and then 1 ml of 1 N $H_2So_4$ was added. The absorbance of each sample at 492 nm was read and is shown in the following table. The results can be expressed as the ratio of the absorbance for the positive control divided by the negative control.

| Sample | Absorbancy at 492 nm | Ratio |
|---|---|---|
| Negative Control | 0.39 | 1.00 |
| Positive Control | 1.18 | 3.03 |

Those publications cited herein are incorporated by reference. Although the foregoing invention has been described in some detail by way of illustration and example for purposes of clarity of understanding, it will be obvious that certain changes and modifications may be practiced within the scope of the appended claims.

What is claimed is:

1. A method for detecting a target nucleic acid sequence in a biological sample comprising:
   a) providing an unpurified biological sample containing a target nucleic acid sequence that is capable of hybridizing with at least one single stranded, labeled nucleic acid probe in a liquid medium, said probe having alone or in combination a length such that when hybridized to the target nucleic acid sequence, the hybridized probe-target complex can be separated from unhybridized probe on the basis of molecular weight, said length being less than 20% of the length of the target;
   b) combining the sample with the labeled nucleic acid probe under hybridizing conditions;
   c) separating unhybridized probe from hybridized probe by gel exclusion chromatography; and
   d) detecting the presence of labeled hybridized probe as a measure of target nucleic acid sequence in the sample.

2. The method of claim 1 wherein the sample is treated with a proteinase prior to step b.

3. The method of claim 2 wherein said proteinase is Proteinase K.

4. The method of claim 1 wherein the sample is denatured by alkaline treatment prior to step b.

5. The method of claim 1 wherein the sample is denatured by thermal denaturation prior to step b.

6. The method of claim 1 wherein the label of said labeled probe is selected from the group consisting of radioisotopes, enzymes, fluorescers, chemiluminescent molecules, radiopaque substances, liposomes, and haptenic molecules.

7. The method of claim 1 wherein a second nucleic acid probe, which hybridizes to a region of the target nucleic acid sequence different from the region to which the labeled nucleic acid probe hybridizes, is combined with the target nucleic acid sequence prior to or during step b.

8. The method of claim 7 wherein said second probe contains a specific binding pair member which permits attachment to another molecule to thereby increase the effective molecular weight of the probe-target complex.

9. The method of claim 7 wherein said second probe is DNA.

10. The method of claim 7 wherein said second probe is RNA.

11. The method of claim 1 wherein said target nucleic acid sequence is a sequence characteristic of a pathogen.

12. The method of claim 11 wherein said pathogen is a virus.

13. The method of claim 12 wherein said virus is selected from the group consisting of hepatitis virus, HIV virus, herpes virus(es), human papilloma virus(es), Epstein-Barr virus, and Cytomegalovirus.

14. The method of claim 11 wherein said pathogen is a prokaryotic cell.

15. The method of claim 11 wherein said pathogen is a eukaryotic cell.

16. The method of claim 1 wherein said nucleic acid sequence for detection is an oncogene.

17. The method of claim 1 wherein said nucleic acid sequence encodes a genetic marker or defect.

18. A method of preparing a single-stranded labeled probe of predetermined desired length, comprising:
   a) purifying a single-stranded template DNA containing a sequence identical to a target sequence;
   b) annealing a nucleic acid primer sequence to the template DNA;
   c) extending the primer sequence by adding Klenow fragment of DNA Polymerase I and nucleotides dATP, dCTP, dGTP and either dUTP or dTTP, wherein at least one of said nucleotides is labeled, and one of said nucleotides is added in a limiting concentration selected to terminate primer extension such that a labeled nucleic acid probe of desired predetermined length range is produced; and
   d) purifying and isolating the nucleic acid probe from step c on the basis of size under denaturing conditions to obtain probes of said predetermined length.

19. The method according to claim 18 wherein said purifying and isolating is performed by chromatography.

20. The method according to claim 19 wherein said chromatography comprises gel exclusion chromatography.

21. The method according to claim 18 wherein said label is selected from the group consisting of radioisotopes, enzymes, fluorescers, chemiluminescent molecules, radiopaque substances and haptenic molecules.

22. The method according to claim 18 wherein prior to step b said template is cloned into host DNA.

23. The method according to claim 22 wherein said vector is single stranded phage DNA.

24. The method according to claim 18 wherein the extending step is carried out at 15° C.

* * * * *

UNITED STATES PATENT AND TRADEMARK OFFICE
CERTIFICATE OF CORRECTION

PATENT NO. : 5,981,171

DATED : November 9, 1999

INVENTOR(S) : Mary C. Kuhns

It is certified that error appears in the above-identified patent and that said Letters Patent is hereby corrected as shown below:

Figure 1
replace "HBV Cenomes"
with --HBV Genomes--.
Col. 1, line 56
replace "Hematology"
with --Hepatology--.
Col. 3, line 3
replace "hepatitis B virus genomes"
with --hepatitis B virus genomes/ml--.
Col. 7, line 55
replace "DATP"
with -- dATP--.
Col. 11, line 40
replace "Absorbancy"
with --Absorbance--.
Col. 1, line 2
replace "host DNA"
with --a vector--.

Signed and Sealed this

Twenty-seventh Day of March, 2001

Attest:

NICHOLAS P. GODICI

Attesting Officer

Acting Director of the United States Patent and Trademark Office